United States Patent [19]

Lindemann

[11] Patent Number: 4,677,971
[45] Date of Patent: Jul. 7, 1987

[54] ADJUSTABLE WRIST SPLINT

[75] Inventor: Peer Lindemann, West Bend, Wis.

[73] Assignee: Rolyan Manufacturing Co. Inc, Menomonee Falls, Wis.

[21] Appl. No.: 813,539

[22] Filed: Dec. 26, 1985

[51] Int. Cl.[4] ............................................. A61F 5/04
[52] U.S. Cl. ....................................... 128/87 R; 128/88
[58] Field of Search ..................... 128/77, 85, 87 R, 88, 128/92 A, DIG. 15, 90; 623/61, 62, 63

[56] References Cited

U.S. PATENT DOCUMENTS

| 2,422,302 | 6/1947 | Horn | 623/61 |
| 3,707,963 | 1/1973 | Keropian | 128/77 |
| 4,437,459 | 3/1984 | Slavetskas | 128/DIG. 15 |

FOREIGN PATENT DOCUMENTS 0191678 12/1905 Fed. Rep. of Germany ........ 128/85

Primary Examiner—Robert A. Hafer
Assistant Examiner—Kathleen D'Arrigo
Attorney, Agent, or Firm—Ira Milton Jones

[57] ABSTRACT

An adjustable wrist splint custom fabricated to fit the forearm and hand of a patient with straps adjustable to fasten the wrist piece to the arm of a patient and pivotal connecting means pivotally connecting the wristpiece to the handpiece to allow universal pivotal movement between the two members. A modification of the device also provides a dynamic splint allowing universal pivoting movement of the joint responsive to actuating forces of the patient.

20 Claims, 9 Drawing Figures

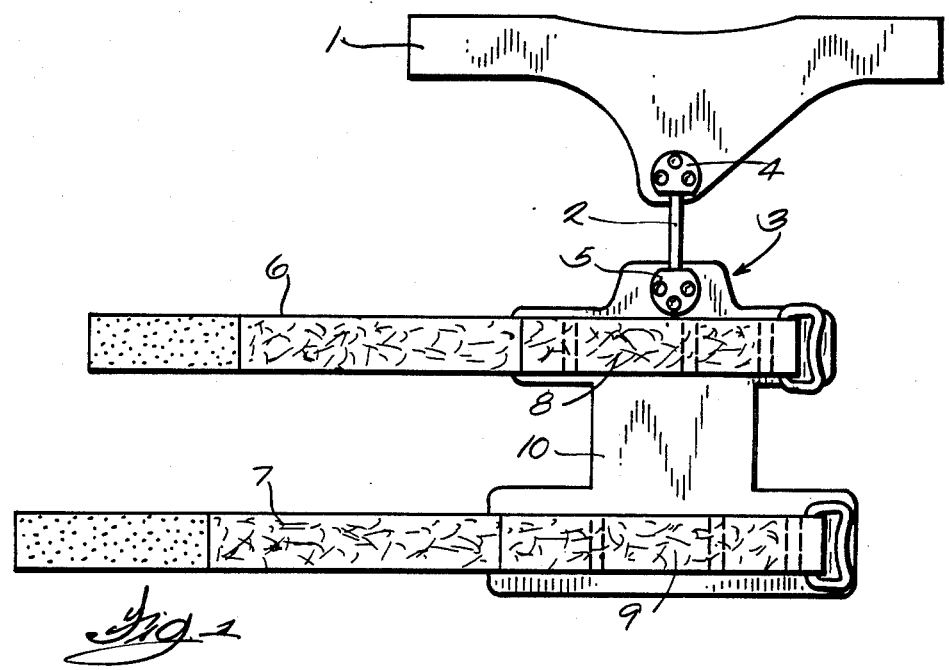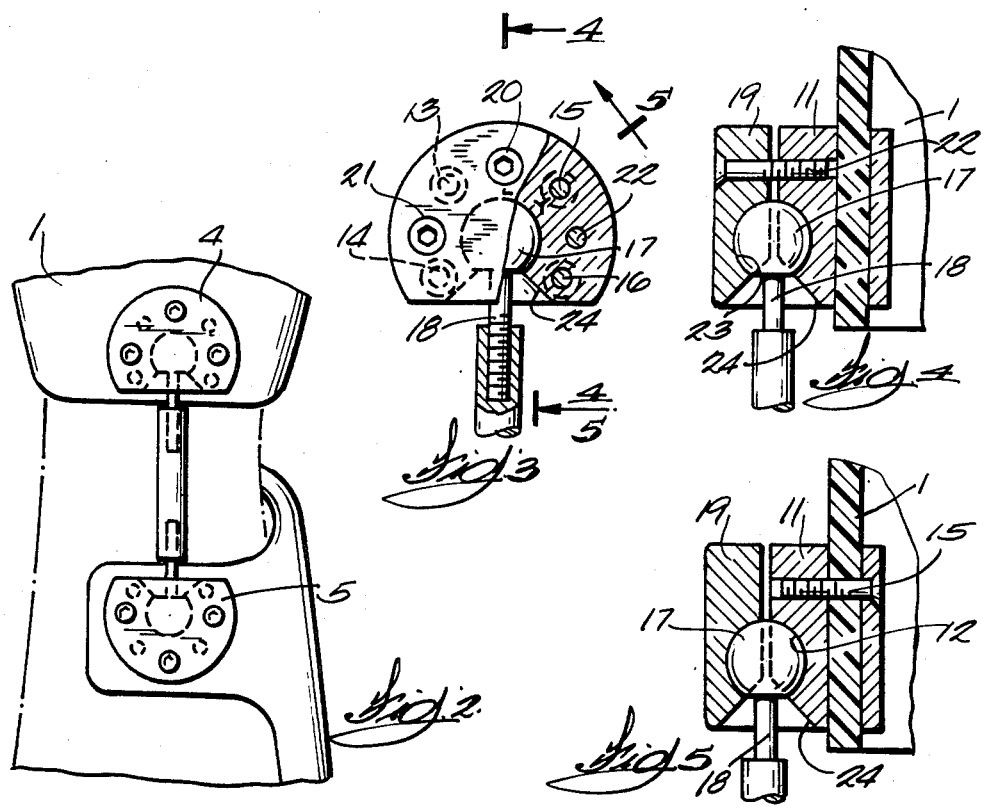

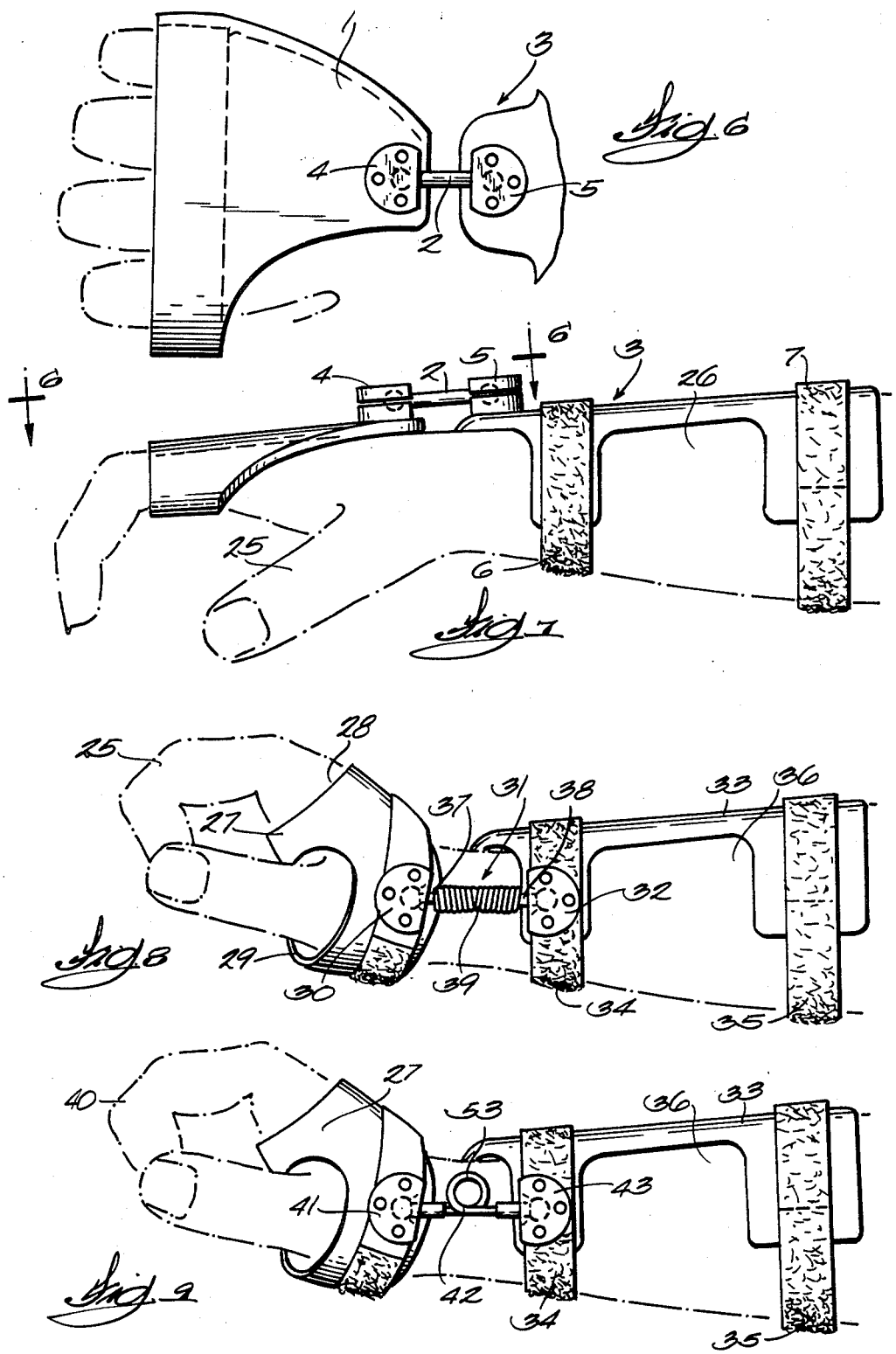

ADJUSTABLE WRIST SPLINT

This invention relates to a wrist splint and, more particularly to an adjustable wrist splint custom fabricated to fit the wrist and hand of a patient and with pivotal means to allow universal pivoting movement between a wristpiece and a handpiece of the splint, and means for locking the pivotal means in a fixed position. A modification provides a dynamic splint in which the pivotal movement is allowed responsive to actuation by forces of the patient.

The wrist and hand of a person comprises a large number of bones and, accordingly, a large number of joints which articulate to allow the movement of the hand or wrist. The mobility of the joints in the hand and wrist are essential to the functions which are normally possible by the hand and wrist. A splint applied to the wrist to assist the wrist in overcoming injury, should allow the maximum mobility possible without causing any pain or further injury to the wrist. In some cases it may be desirable to regularly maintain the strength and range of motion of the joints even though a splint is used on the wrist which may partially limit the motion of the joints. The mobility of the wrist may be maintained through regular exercising of the wrist for a limited period of time, in a splint which may allow this movement. The use of a dynamic splint allows motion responsive to an actuating force in the wrist. This may be accomplished if the motion is medically acceptable and will not cause further injury to the wrist.

One of the goals of therapy is to help people function as independently as possible. Accordingly, a hand should be splinted in a functional position if at all possible. This permits the patient to perform normal tasks with the splint in place, depending on the type of splint used.

Upper limb orthoses serve one or more of the basic functions such as assisting the residual weakened motive power or substitute appropriate mechanism for the loss of the motivating force. They protect the injured portion of the wrist or hand from pain or potential deformity. They also correct an existing deformity pending the type of disability. Restoration of the hand function is of primary importance in the management of the upper limb. The splint may be used for splinting of the ligament, for ligament repair of the wrist, total wrist implant, coupal fractures, serial adjustment of the wrist motion, splinting following nerve injuries, substitution wrist patterns, and as a working splint for carpal tunnel syndrome. Accordingly, the applicant has provided for an adjustable wrist splint designed to be custom fabricated for each patient. The wristpiece and handpiece may be formed of a thermo-plastic material which is deformable to be fitted to the hand and wrist of the patient.

For the purpose of demonstration, the material may be heat-sensitive to allow molding of the splint to fit the contour and shape of the hand so that the patient can wear the splint with comfort. Once the splint is formed to fit the hand and wrist, a cushion inner lining is fitted on the inside of the mold to provide a soft bearing surface for the forearm and hand of a patient. Attached to these two members are pivotal joints with a connecting link which may be of any desired length and adjustable by an adjustable mechanism in the link per se.

A dynamic splint can be provided in which the joint is flexible responsive to actuating force of the patient's hand. Two self-adhesive D-ring straps are provided for attaching to the forearmpiece and allowing adjustable fastening means by the straps as they embrace the wrist of the patient.

The link and joints connecting the forearmpiece with the handpiece may be of any suitable length and may be adjustable to the desired length and position or may comprise a dynamic link allowing movement of the link and joints during normal operation by the patient.

It is an object of this invention to provide an adjustable splint with means for varying the length of the link between the forearmpiece and the handpiece of the splint.

It is another object of this invention to provide an adjustable splint with means for varying the length and position of the forearmpiece relative to the handpiece and means for fixing the desired position of these two members.

It is a further object of this invention to provide an adjustable dynamic splint with means for varying the length and position of the forearmpiece relative to the handpiece responsive to an actuating force from the patient, and means for returning the two members to a rest or neutral position.

The objects of this invention are accomplished through the use of a forearmpiece which is preformed and also a handpiece which is also preformed. These two members may be constructed of a thermo-plastic material which is deformable as, for example, the heat sensitive material which upon heating the material can be custom fabricated to fit the forearmpiece and the hand of the patient. Upon fitting the forearmpiece and the handpiece to the patient, a cushioning material is applied to the inside surface of the two members to soften the bearing surface engaging the patient. Two straps fastened to the forearmpiece can then be adjustably tightened to embrace the wrist of the patient to fasten the splint to the patient's arm in its normal operating position. The forearmpiece and the handpiece are preferably connected by a double jointed linkage arrangement with a ball joint on each end of the link with each ball joint fastened to one of the forearmpiece or handpiece. The ball joint can be adjustably tightened or loosened to provide a fixed or a movable joint thereby adjusting the length between the two members or the relative position between the two members as desired.

A dynamic splint can be provided whereby the link per se is constructed of a resilient material which normally returns to a neutral position, but can be displaced relative to this neutral position responsive to a force initiated by the patient. This allows relative movement of one or more joints of the patient as is desired.

Referring to the drawings, the preferred embodiment of the invention is illustrated.

FIG. 1 illustrates an assembled view of the adjustable splint prior to forming and fitting the splint to the patient's arm.

FIG. 2 is an enlarged view of the link and double ball joints connecting the forearmpiece with the handpiece.

FIG. 3 is a partially section view of a ball joint and a portion of the link.

FIG. 4 is a section view taken on line 4—4 of FIG. 3.

FIG. 5 is a cross section view taken on line 5—5 of FIG. 3.

FIG. 6 is a plan view or dorsal aspect as taken on lines 6—6 of FIG. 7.

FIG. 7 is a side view of the adjustable splint with the dorsal mounting of the link and pivotal joints.

FIG. 8 is a side view of the adjustable splint with an adjustable link pivotally connecting the two ball joints on the forearmpiece and handpiece.

FIG. 9 is a side view of the adjustable dynamic splint with a resilient link universally connected in the pivotal ball joint on the wristpiece and on the handpiece.

Referring to the drawings, FIG. 1 illustrates the assembled view of the adjustable splint. The handpiece 1 is preferably constructed of a deformable material such as Balata, which is heat-sensitive and can be heated in warm water and then deformed to a desired shape and configuration such as the shape of a patient's hand or wrist. The handpiece 1 is connected by a link 2 to the forearmpiece 3. Each end of the link is connected through a ball joint 4 and 5. The ball joints allow universal pivotal movement between the link 2 and the handpiece 1 or the forearmpiece 3. The forearmpiece 3 carries the adjustable straps 6 and 7. Each of the adjustable straps is constructed with a pressure-sensitive self adhesive surface which is normally covered by a tape which can be removed and then the adhesive pressure-sensitive surface is pressed against the side of the forearmpiece 2 to fasten the strap in the desired position, as shown.

The area of the adhesive surface is the underside of the area 8 and 9 of straps 6 and 7. The tape is peeled off and then the strap is pressed against the outer surface 10 of the wristpiece 3.

Referring to FIG. 2, the ball joint 4 and ball joint 5 are shown in an enlarged view. Handpiece 1 is fastened to the ball joint by the screws extending through the handpiece into the housing 11 which forms a hemispherical socket 12. A plurality of screws 13, 14, 15 and 16 extend through the handpiece 1 into the housing 11 to fasten the handpiece and housing together. The ball 17 of the link end 18 seats in the hemispherical socket 12. Similarly, the housing 19 is fastened together with the housing 11 by the three screws 20, 21 and 22. The housing 19 is formed with the hemispherical socket 23 which also receives a portion of the ball 17 on the link end 18. Each of the housings 11 and 19 is formed with a forty-five degree (45°) opening 24 which allows pivotal movement of the link 18 in a universal manner in any direction.

FIG. 6 illustrates a plan view of and FIG. 7 illustrates a side view of the pivotal connecting link between the handpiece 1 and the forearmpiece 3.

The hand 25 is shown in the handpiece 1 and the wrist 26 is shown in the forearmpiece 3 in these views. The forearmpiece 3 is shown in the dorsal position embracing the back sice of the arm, while the straps 6 and 7 embrace the forearm. The link 2 is a fixed link and, as shown, is only adjustable in the two ball joints 4 and 5. The ball joints are adjustable by loosening the screws which tighten or loosen the housings against the ball of the ball joint. The screws can be tightened to provide a fixed position in any position desired to adjustably preset a position of the hand relative to the forearm.

FIGS. 8 and 9 show a modified handpiece 27 with a provision for an opening 28 for the fingers of the hand and an opening 29 for the thumb. This handpiece gives more support to the hand than the handpiece shown in FIGS. 6 and 7. The handpiece 27 carries a ball joint 30 pivotally connected to the link 31 which, in turn, is also pivotally connected to the joint 32 and to the forearmpiece 33. The forearmpiece 33 is fastened by means of the straps 34 and 35 to the forearm 26 of the patient. The link 31, as shown, is adjustably axially. The link 31 consists of a threaded endpiece 37 and a threaded endpiece 38 threadedly engaging the internal threads of the sleeve 29 which is knurled on its outer periphery to provide rotation of the sleeve clockwise or counterclockwise to extend or contract the link 31.

FIG. 9 illustrates a dynamic adjustable splint. The handpiece 27 is fitted to the hand 40. The forearmpiece 33 is also fitted to the forearm 36 and fastened by means of the straps 34 and 35. The ball joint 41 pivotally connects the link 42 to the handpiece 27. A ball joint 43 pivotally connects the link 42 to the forearmpiece 33. The link 42 includes a resilient coil 53 which allows flexing of the handpiece 27 relative to the forearmpiece 33 responsive to an actuating force of the patient. Normally the link 42 will return to a neutral position, as shown in FIG. 9.

The operation of the adjustable splint will be described, as follows:

FIG. 1 illustrates the adjustable splint in its assembled position. Prior to fabrication the straps 6 and 7 each contain a tape on the backside of the area 8 and 9 of the straps. This tape is removed and an adhesive which is pressure sensitive is then pressed against the outside of the forearmpiece 10 in the position as shown. This automatically bonds the strap to the forearmpiece in the position as shown. Each of the links 2 is fastening in position by means of the four screws 13, 14, 15 and 16. The screws extend through openings in the handpiece 1 and threadedly engage openings as illustrated in FIG. 2. Each screw is adapted for an Allenhead slot to receive an Allenhead wrench by which the screw is threadedly tightened in the position as shown. This fastens the housing 11 onto the handpiece 1. Similarly, the screws 20, 21 and 22 are fastened in openings, as shown in FIG. 4 and tightened by means of an Allenhead wrench in the socket, as shown in FIG. 3.

Tightening of the housing 19 with housing 11 clamps down on the ball 17 to lock the assembly in place. The tightening of the socket controls the adjustability of the link relative to the handpiece. Similarly, the joint 5 is also fastened to the forearmpiece 10 and tightened by housings to lock the joint 5 or loosen it to permit adjustment as desired. Accordingly, the splint can be adjusted by movement of the link realtive to handpiece 1 or the forearmpiece 3.

Referring to FIGS. 6 and 7, the link can be adjusted allowing relative pivotal moveent between the handpiece 1 and the forearmpiece 3. FIGS. 8 and 9 illustrate a side mounting of the link and the link can be adjusted to permit relative movement between the handpiece 27 and the forearmpiece 33. A single link 31 on the side, as shown, can be used or two links 31 with a link on each side of the wrist may also be used to provide additional support between the forearmpiece 33 and the handpiece 27. Likewise, one or two links can be used in the adjustable splint shown in FIG. 9. These links can be adjusted by tightenting or loosening of the joints 30 and 32 and axially adjusted by rotating the sleeve 39 on the link 31.

The dynamic link 42 can be positioned in any neutral position desired. Relative movement between the handpiece 27 and the forearmpiece 23 is permitted by the resilient coil 53 in the link. This coil will allow relative movement of the wrist joint responsive to activation by the patient. This device allows greater movement of the wrist and does not lock the wrist in a fixed position as does prior art links.

The embodiments of the invention in which an exclusive property or privilege is claimed are defined as follows:

1. An adjustable wrist splint including a selectively positioned and supported handpiece in a selected one of a plurality of positions on a forearmpiece comprising:
   a cushioned forearmpiece;
   a cushioned handpiece;
   a single link pivotally connected to said forearmpiece and to said handpiece and supporting said handpiece to selectively allow universal pivotal movement between said pieces;
   said handpiece including means for embracing a hand;
   said forearmpiece including means for embracing a forearm;
   said link including at least one universal pivotal and lockable joint to selectively allow universal pitoval movement between said forearmpiece and said handpiece; and
   readily adjustable tightening means in said universal pivotal joint to selectively lock said joint and prevent pivotal movement of said joint and fixedly support said handpiece on said forearmpiece.

2. An adjustable wrist splint as set forth in claim 1, wherein
   said link defines a resilient structure to allow flexing between said handpiece and said forearmpiece.

3. An adjustable wrist splint as set forth in claim 1, including
   means fastening said link on the side of said handpiece and said forearmpiece.

4. An adjustable wrist splint including a selectively positioned and supported handpiece on a forearmpiece comprising:
   a cushioned forearmpiece,
   a cushioned handpiece,
   a link pivotally connecting said forearmpiece and said handpiece and supporting said handpiece,
   a universal pivotal joint pivotally connecting said link to said forearmpiece for selective universal pivotal movement relative to each other,
   a universal pivotal joint pivotally connecting said link to said handpiece for selective universal pivotal movement relative to each other,
   tightening means in each of said joints locking each of said joints in an adjusted locked position and fixedly supporting said handpiece on said forearmpiece,
   means on said handpiece for embracing a hand, and fastening means on said forearmpiece for embracing and fastening said forearmpiece to a forearm.

5. An adjustable wrist splint as set forth in claim 4, wherein said fastening means includes straps adjustably fastening said wrist splint to a forearm.

6. An adjustable wrist splint as set forth in claim 5, including
   Velcro fastening means on said straps to adjustably position said straps for embracing the forearm and fastening said wrist splint.

7. An adjustable wrist splint as set forth in claim 5, including
   bonding means for bonding said straps to said forearmpiece.

8. An adjustable wrist splint as set forth in claim 4, wherein said link includes
   a threaded endpiece connected to said handpiece, said threaded endpiece connected to said forearm piece,
   a threaded sleeve threadedly engaging said endpieces to provide axially adjustable movement of said link.

9. An adjustable wrist splint as set forth in claim 4, including
   resilient means forming said link interconnected between said forearmpiece and said wristpiece to provide a dynamic link resiliently flexing to allow movement between the forearmpiece and said handpiece responsive to an activating force from a wrist or hand.

10. An adjustable wrist splint as set forth in claim 2, including
    means connecting said forearmpiece to said handpiece on the dorsal side of said pieces to allow pivotal movement between said forearmpiece and said handpiece.

11. An adjustable wrist splint as set forth in claim 4, including
    at least two links pivotally connecting said forearmpiece with said handpiece to provide universal pivotal movement between said pieces.

12. An adjustable wrist splint as set forth in claim 4, whereby
    said link is resilient and is approximately aligned with the wrist joint between the hand and said forearm, said resilient link allowing the wrist joint to pivot with said link.

13. An adjustable wrist splint as set forth in claim 4, whereby
    said pivotal joint defines ball joints, said tightening means defines screws means for tightening and loosening said ball joints to allow greater or lesser friction in said joints to maintain said joints in rigid position or allow said joints to pivot.

14. An adjustable wrist splint as set forth in claim 4, wherein
    said pivotal joints defining ball joints with means for assembling and tightening said joints to maintain said joints in a fixed position to fix the relative position of said handpiece relative to said forearmpiece.

15. An adjustable wrist splint as set forth in claim 4, wherein
    said pivotal joints define ball joints, and said tightening means define screws and threaded openings for tightening said ball joints to prevent pivoting of said pivotal joints.

16. An adjustable wrist splint as set forth in claim 4, wherein
    said pivotal joints defining ball joints each including, a ball, housings forming two hemispherical recesses, said tightening means tightening said housings and the ball in said joints to vary the friction and ease of pivoting said joint.

17. An adjustable wrist splint as set forth in claim 4, including
    straps for embracing said forearm for fastening said wrist splint to a forearm.

18. An adjustable wrist splint as set forth in claim 4, including
    straps for embracing a forearm and the forearmpiece for fastening said wrist splint to the forearm, said forearmpiece and said handpiece including thermoplastic material allowing said pieces to be deformably fitted to a hand and the forearm of a patient for fabricating the wrist splint to the arm and hand of the patient.

19. An adjustable wrist splint including a selectively positioned and supported handpiece on a forearmpiece comprising:
   a forearmpiece,
   a handpiece
   cushioning means fitted to said forearmpiece to provide a soft surface for the forearm and cushioning means fitted to said handpiece to provide a soft hand surface,
   a link including a universal pivotal joint on each end providing selective universal pivotal movement between said link and said forearmpiece and said handpiece,
   compressible tightening means on each of said joints selectively locking the relative position in one of a plurality of positions of said link and forearmpiece and handpiece and preventing any pivotal movement of the joints and fixedly supporting said handpiece on said forearmpiece,
   means on said handpiece for embracing a hand, and adjustable fastening means on said forearmpiece for fastening said forearmpiece to a forearm.

20. An adjustable wrist splint as set forth in claim 3, including
   means bonding the cushioning means on the inner surface of said handpiece and said forearmpiece,
   said handpiece and forearmpiece defining a molded inner surface to fit the hand and forearm.

* * * * *